(12) United States Patent
Melamed

(10) Patent No.: US 10,338,018 B2
(45) Date of Patent: *Jul. 2, 2019

(54) SYSTEM, DEVICE AND METHOD FOR TESTING AN OBJECT

(71) Applicant: VAYYAR IMAGING LTD., Yehud (IL)

(72) Inventor: Raviv Melamed, Nes Ziona (IL)

(73) Assignee: VAYYAR IMAGING LTD, Yehud (IL)

( * ) Notice: Subject to any disclaimer, the term of this patent is extended or adjusted under 35 U.S.C. 154(b) by 10 days.

This patent is subject to a terminal disclaimer.

(21) Appl. No.: 15/838,575

(22) Filed: Dec. 12, 2017

(65) Prior Publication Data

US 2018/0100819 A1 Apr. 12, 2018

Related U.S. Application Data

(63) Continuation of application No. 15/115,996, filed as application No. PCT/IL2015/050126 on Feb. 4, 2015, now Pat. No. 9,964,505.

(Continued)

(51) Int. Cl.
*G01N 27/02* (2006.01)
*G01N 22/02* (2006.01)
*G01N 33/04* (2006.01)

(52) U.S. Cl.
CPC ........... *G01N 27/025* (2013.01); *G01N 22/02* (2013.01); *G01N 33/04* (2013.01)

(58) Field of Classification Search
CPC ......... G01N 22/04; G01N 33/04; G01S 13/04
See application file for complete search history.

(56) References Cited

U.S. PATENT DOCUMENTS

| 4,010,715 A | 3/1977 | Robar et al. |
| 4,211,224 A | 7/1980 | Kubach |

(Continued)

FOREIGN PATENT DOCUMENTS

EP 1845364 A2 10/2007

OTHER PUBLICATIONS

Crocco L et al: "Early-stage leaking 1-13 pipes GPR monitoring via microwave a tomographic inversion" Journal of Applied Geophysics. Elsevier. Amsterdam. NL. vol. 67. No. 4. Apr. 1, 2009 (Apr. 1, 2009). pp. 270-277. XP026033856.

(Continued)

*Primary Examiner* — Jermele M Hollington
*Assistant Examiner* — Alvaro E Fortich
(74) *Attorney, Agent, or Firm* — Browdy and Neimark, PLLC

(57) ABSTRACT

A system and method for characterizing non-solid substances, the system comprising a housing body having a cavity therein the cavity is configured to contain said substances; a transmit/receive unit configured to generate and transmit Radio Frequency (RF) signals; at least one electromagnetic sensor attached to said housing body and said transmit/receive unit, wherein said sensor is configured to provide RF responses data of said substances; a Radio Frequency Signals Measurement Unit (RFSMU) configured to receive said RF responses and measure said RF responses; and a processor connected to said sensor said processor is configured to process said responses to identify the characteristics of said substances.

20 Claims, 7 Drawing Sheets

Related U.S. Application Data

(60) Provisional application No. 61/935,873, filed on Feb. 5, 2014.

(56) References Cited

U.S. PATENT DOCUMENTS

| | | | |
|---|---|---|---|
| 5,101,163 | A | 3/1992 | Agar |
| 5,718,208 | A | 2/1998 | Brautigan |
| 5,829,522 | A | 11/1998 | Ross et al. |
| 6,293,142 | B1 * | 9/2001 | Pchelnikov ............ G01F 23/284 324/640 |
| 2002/0165295 | A1 | 11/2002 | Matsumoto |
| 2006/0220658 | A1 | 10/2006 | Okamura |
| 2006/0255276 | A1 | 11/2006 | Manneschi |
| 2008/0296306 | A1 | 12/2008 | Handa |
| 2009/0114812 | A1 * | 5/2009 | Landgraf ............. G01N 27/622 250/282 |
| 2011/0068807 | A1 | 3/2011 | Kesil et al. |
| 2011/0199097 | A1 * | 8/2011 | Hartsough ............... A61B 5/05 324/629 |
| 2011/0023793 | A1 | 9/2011 | Melamed et al. |

OTHER PUBLICATIONS

Ayliffe et al., 'Electric Impedance Spectroscopy' Using Microchannels with Integrated Metal Electrodes IEEE Journal of Microelectromechanical Systems, vol. 8, No. 1, Mar. 1999.

Valerie Favry, "Design and Development of a Novel Electronic Sensor for Detecting Mastitis Based on Conductance/Impedance Measurements", Thesis submitted for the Degree of Master of Science,Supervised by Prot Dermot Diamond School of Chemical Sciences, National centre for Sensor Research Jul. 2004.

Pallavi R. Malamel et al., "Microwave Reflectometry Based Electrical Characterization of Milk for Adulteration Detection", Advance in Electronic and Electric Engineering, ISSN 2231-1297, vol. 4, No. 5 (2014), pp. 487-492.

* cited by examiner

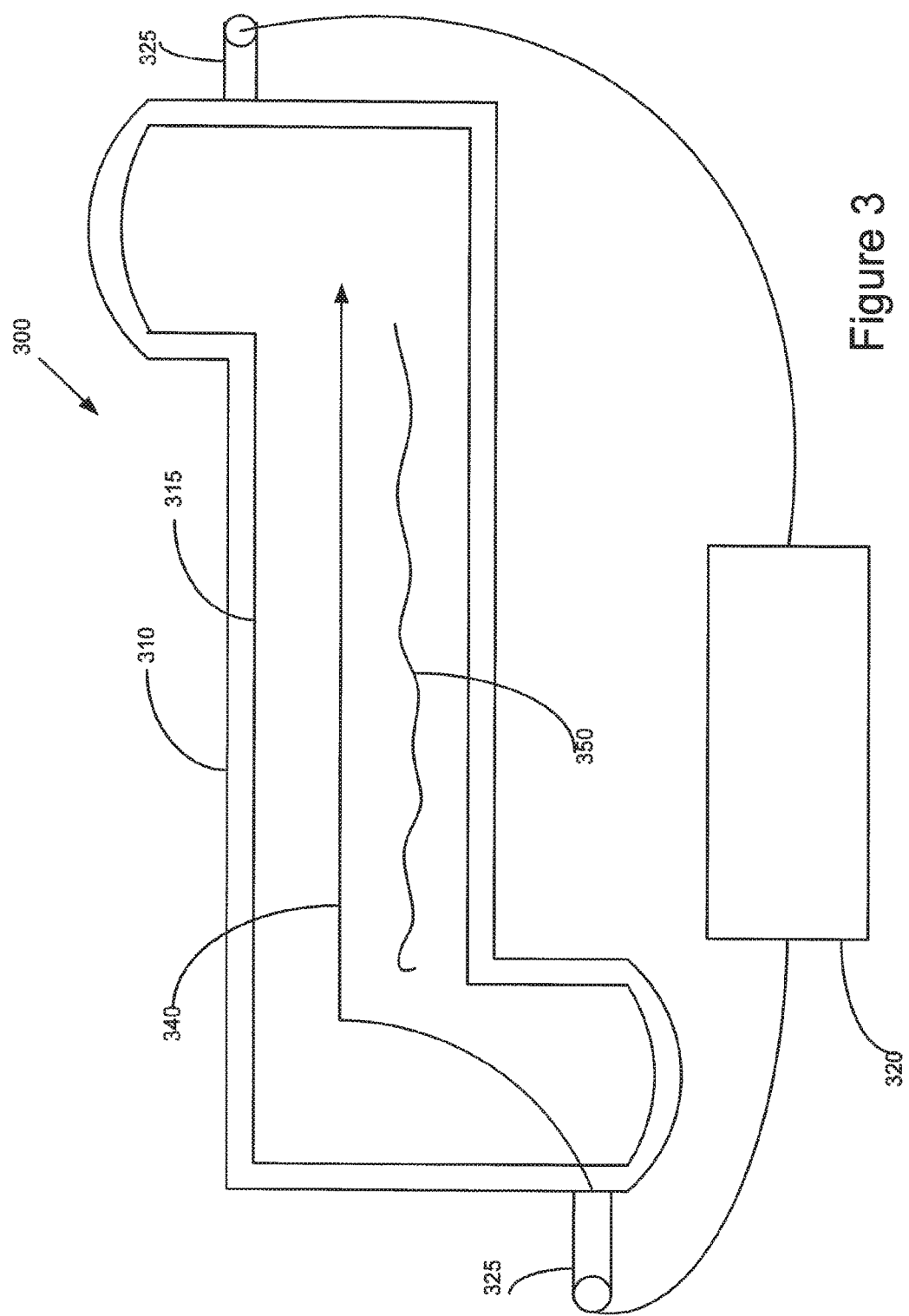

SYSTEM, DEVICE AND METHOD FOR TESTING AN OBJECT

FIELD OF THE INVENTION

The present invention relates to a sensing system device and method for testing an object or substances and more specifically, but not exclusively, to testing a liquid or ointment using Radio Frequency (RF) sensors such as microwave sensors.

BACKGROUND

From time immemorial there was a need to recognize and diagnose substances or objects to identify if they have been tampered with or adulterated. Immediate and precise identification of objects under examination are configured to recognize defects, forgery or diseases in the substances.

For example in the agriculture field there is a constantly need to recognize defects and diseases of agriculture products like fruits and vegetable, and more commonly in products such as milk, juice etc.

For example Mastitis, inflammation of the mammary glands of dairy cows, remains one of the costliest diseases in cattle and its early detection remains a major goal of the dairy industry. It has been established that currently available commercial devices do not appear to be sensitive enough to detect mastitis accurately on-line. The prior art solutions that are currently used to detect mastitis are based on the fact that mastitis causes changes in the conductivity of milk, by damaging the mammary membrane leading to alteration of the balance of sodium, potassium and chloride ions. Previous studies have demonstrated that these changes in milk conductivity can be used as a direct indicator of the presence and degree of mastitis infection.

In the past, the herd person usually noticed the appearance of the first clinical symptoms of mastitis on the animal. Nowadays, the detection of abnormal milk is required before milking according to the EU directive: "Before milking of the individual cow, the milker must inspect the appearance of the milk. If any physical abnormality is detected, milk from the cow must be withheld from delivery to the dairy". Therefore, foremilk of each animal is now visually examined directly in the parlour using a strip cup or a plate. However, as no symptoms are really obvious, farmers or herdspersons rarely identify the primary signs during a routine inspection or during milking in individual cows. Hence, the biochemical properties of milk turn out to be very useful in order to evaluate the cow's metabolic status, in particular, the udder condition. In the last few decades, a variety of cow side tests and laboratory tests have been developed for detecting mastitis such as the strip cup test, the California Mastitis Test, etc. Thanks to these methods of detection, foremilk control is usually followed by owners of small herds, but it takes a lot of time and money for large herds.

Currently available in-line mastitis detectors are fitted to the long milk tube. They have a wire mesh filter through which milk passes. Mastitis clots clog the filter and clot-free milk is able to pass through the filter.

A variety of diagnostic tests for mastitis are available and are used as indicators of udder inflammation. They cannot, however, assess the degree of infection accurately. As the name indicates they are performed directly on the animal. These experiments are useful to indicate suspect samples but they cannot be accepted as definitive procedures as many false positives cases remain.

One of the solutions to overcome such problems, are described in the prior art, for example, in an article entitled "DESIGN AND DEVELOPMENT OF A NOVEL ELECTRONIC SENSOR FOR DETECTING MASTITIS BASED ON CONDUCTANCE/IMPEDANCE MEASUREMENTS" by Valerie FAVRY, another article relating to adulteration detection entitled "Microwave Reflectometry Based Electrical Characterization of Milk for Adulteration Detection" by Pallavi R. Malamel, Tapas K. Bhuiya and Rajiv K. Gupta.

Other fields where a substance diagnose process is required may be for example to examine a spillage found in proximity to a water, gasoline or oil pipeline or tank as a good indication of the severity of water or gasoline leakage in a distribution network.

There are various techniques reported in the literature for leak detection such as a) Acoustic leak detection methods utilizing devices such as aquaphones or geophones to listen for leaks on the ground above the pipes b) acoustic correlation methods c) infrared thermography, tracer gas technique and ground-penetrating radar (GPR) d) Magnetic Flux Leakage (MFL) based detectors ultrasound (UT) to search for pipe defects.

SUMMARY OF INVENTION

It is an object of the present invention to provide a system, device and method for characterizing substances such as non-solid substances wherein the substances are not in direct contact with the system sensing equipment.

It is yet another object of the present invention to provide a system and method that will allow obtaining information, for example but not limited to, testing of an object such as milk, ink or drug to see if it has been adulterated.

According to a first aspect of the invention there is provided a system for characterizing non-solid substances, the system comprising: a housing body having a cavity therein wherein said cavity is configured to contain said substances; a transmit unit configured to transmit a plurality of Radio Frequency (RF) signals; at least one electromagnetic sensor connected to said housing body and said transmit unit, wherein said sensor is configured to provide RE responses data of said substances; a Radio Frequency Signals Measurement Unit (RFSMU) configured to receive said RF responses and measure said RE responses; and a processor connected to said sensor said processor is configured to process said responses to identify the characteristics of said substances.

In an embodiment e sensor comprises at least two antennas and wherein the processor is configured to analyze a passage of energy transmitted from at least one of said antennas to at least one other antenna.

In an embodiment, the sensor is a capacitive sensor and wherein the sensor is configured to spatially resolve the dielectric properties of the substances.

In an embodiment, the capacitive sensor comprises: a plurality of sensing feed lines; a plurality of sensing plates; and a plurality of receive lines wherein each of the plurality of feed lines is coupled to at least one corresponding receive line through an electromagnetic field formed between at least two sensing plates connected to the feed and receive lines and the substances.

In an embodiment, the sensor is selected from the group consisting of: an antenna array, a MIMO radar sensor, resonant cavity sensor, microwave sensor, waveguide sensor.

In an embodiment, the MIMO radar sensor comprises a wideband antenna array connected to the transmit unit, said transmit unit is configured to generate microwave signals to said antenna array.

In an embodiment, the RF responses data comprises impedance measurements.

In an embodiment, the housing body is selected from a group consisting of:
  a pipe, a pipeline, a bottle, a test tube, a permeable tube, a non-permeable tube an open lab tube, a closed lab tube.

In an embodiment, the permeable tube comprises a granular material configured to receive said substance penetrating said tube.

In an embodiment, the tube comprises an inlet pipe and outlet pipe.

In an embodiment, the sensor is attached externally to the housing body walls.

In an embodiment, the sensor is attached internally to the housing body.

In an embodiment, the substances are selected from the group consisting of: liquid, paste, gas.

In an embodiment, the liquid is selected from the group consisting of:
  oil, milk, ink, water, bodily fluids.

In an embodiment, the sensor in not in direct contact with said substance.

According to a second aspect of the present invention there is provided a method for characterizing non-solid substances, said method comprising: obtaining multiple RadioFrequency (RF) signals from one or more RF sensors, said RF sensors are attached to a housing body or to a cavity of said housing wherein said cavity is configured to contain said substances; measuring the obtained RF signals by a Radio Frequency Signal Measurement Unit (RFSMU), wherein said RFSMU is connected to said sensors; and processing said measured RF signals by a processor to identify the characteristics of said substances.

In an embodiment, the method comprises processing the obtained multiple RF signals to measure the dielectric properties of said substances.

In an embodiment, the method comprises: comparing the dielectric properties of said substances to a predefined threshold reference to identify abnormal characteristics in said substances.

In an embodiment, the properties of the substances are spatially resolved.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to he necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks, according to embodiments of the invention, could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein, are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The subject matter disclosed may best be understood by reference to the following detailed description when read with the accompanying drawings in which:

FIG. 3 depicts the testing system including a waveguide, according to an embodiment of the invention;

DETAILED DESCRIPTION

The present invention relates to a sensing system and method for testing an object and more specifically, but not exclusively, to characterizing a liquid or ointment using RF sensors such as microwave sensors. The present invention further provides a system and method for analyzing or characterizing an object for example according to impedance measures or dielectric properties of said object using one or more sensors which are not in direct contact the object.

According to some embodiments of the invention a microwave sensor transmits microwaves towards a detection area and senses an object within that area through the reflection and modulation of the microwaves, for example by a Doppler effect from said object located in the detection area.

Figure 1:
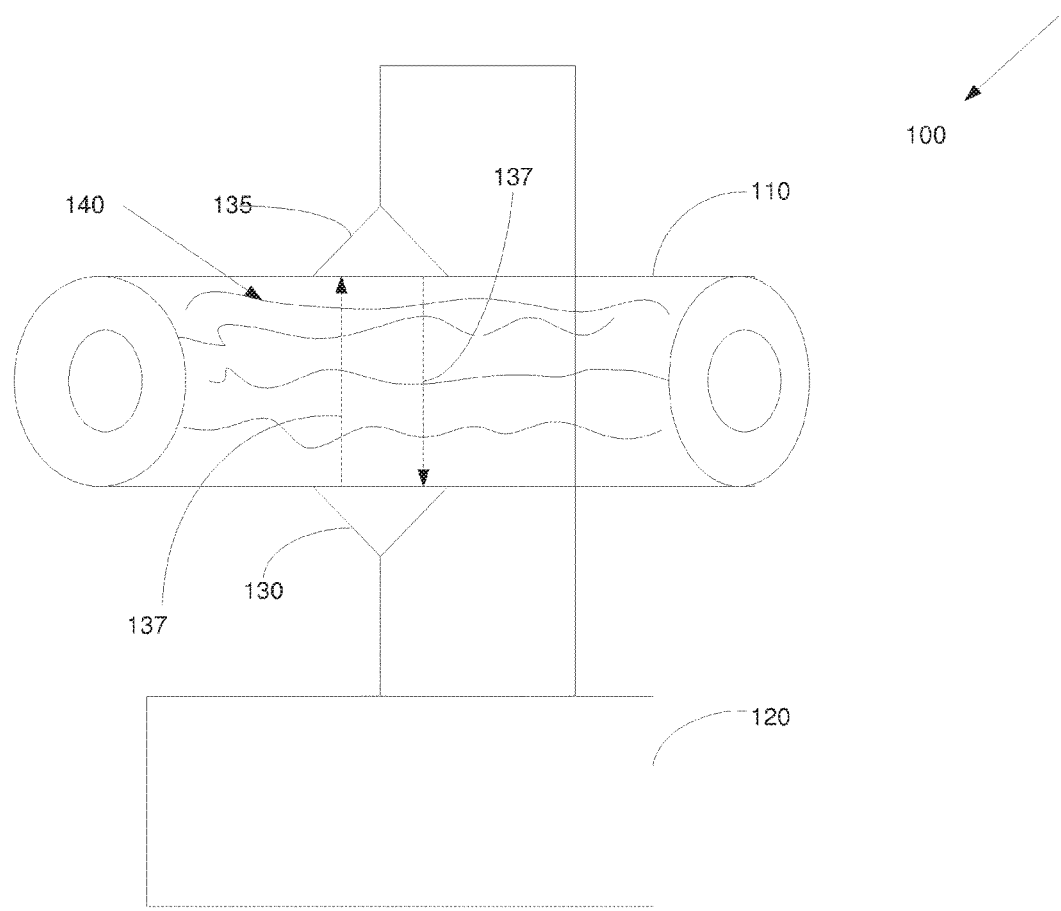
FIG. 1 is schematic view of a testing system including an antenna attached or mounted on a container, according to an embodiment of the invention.

The present embodiments may be placed at gas stations for example in proximity to a gasoline tank or inside a pipeline for characterizing of spillage such as liquid spillage, resulted for example of a gasoline pipeline or tank leakage. Referring now to the drawings, FIG. 1 illustrates a testing system 100 configured to characterize a substance e.g. the inside of an object-under-test (OUT) 140 and to identify any change in the ingredients of the OUT. For example the testing device may identify the components e.g. the type and amount) found within a liquid or ointment. The results identified by the testing device 100 may be transmitted, displayed or shared to one or more users, for example in real-time, through various media, such as mobile telephone or close loop TV system.

According to one embodiment of the invention, the system 100 may include a container, housing or vessel 110 holding the OUT 140. The container may be in the shape of a pipe or any shape capable of holding the OUT 140. The container or pipe 110 may be connected to the OUT source via one or more inlet and outlet pipes. For example the container may be part of or may be connected via the inlet pipe to a milking system and the OUT may be milk received directly from the milking system. The system may include one or more microwave sensors such as antenna sensors 135 and 130 attached to or located in proximity to the container 110. The sensors may transfer a plurality of RE signals propagating a wave into the container 110 for characterizing the OUT. The system includes a transmit/receive subsystem not shown) configured to generate and transmit the RF signals, a Radio Frequency Signals Measurement Unit (RF-SMU) 120 such as a Vector Network Analyzer (VNA) for measuring the received/reflected signals, a data acquisition subsystem and further a processor unit for processing the measured signals and characterising the OUT.

According to one embodiment of the invention as shown in FIG. 1 sensors 135 and 130 are externally connected to the container 110 walls to generate a plurality of signals 137 penetrating the container walls from both sides and examining the OUT. Thus, enabling a sterilized measuring process and preventing the direct contact between the OUT and the antenna, and avoiding unwanted external substances such as dirt to influence the measurement process.

In one embodiment, the sensors such as sensors 135 anti 130 may be multi-layer structure implemented at least in part with printed circuit board techniques using appropriate dielectric materials. Commonly used materials arc glass-epoxy, Teflon-based materials. Layers of high-dielectric-constant materials can be incorporated in order to match the antennas to materials under test.

According to one embodiment of the invention, the sensors 135 and 130 may include one or more antennas such as antenna array. The antennas can be of many types known in the art, such as printed antennas, waveguide antennas, dipole antennas or "Vivaldi" broadband antennas. The antenna array can be linear or two-dimensional, flat or conformal to the region of interest.

The transmit/receive subsystem is responsible for generation of the RF signals, coupling them to the antennas, reception of the RF signals from the antennas and converting them into a form suitable for acquisition. The signals can be pulse signals, stepped-frequency signals, chirp signals and the like. The generation circuitry can involve oscillators, synthesizers, mixers, or it can be based on pulse oriented circuits such as logic gates or step-recovery diodes. The conversion process can include down conversion, sampling, and the like. The conversion process typically includes averaging in the form of low-pass filtering, to improve the signal-to-noise ratios and to allow for lower sampling rates.

According to some embodiments of the invention, the transmit/receive subsystem may perform transmission and reception with multiple antennas at a time or select one transmit and one receive antenna at a time, according to a tradeoff between complexity and acquisition time.

The data acquisition subsystem collects and digitizes the signals from the transmit/receive subsystem while tagging the signals according to the antenna combination used and the time at which the signals were collected. The data acquisition subsystem will typically include analog-to-digital (A/D) converters and data buffers, but it may include additional functions such as signal averaging, correlation of waveforms with templates or converting signals between frequency and time domain.

The processing unit is responsible for converting the collected signals into responses characterizing the OUT, and performing the algorithms for converting the sets of responses, into data relating to the OUT characteristics. According to one context of the invention described herein, the processor is responsible for Doppler processing as well, in which changes in the response over time are taken into account along with the response itself. The data processing unit is usually implemented as a high-performance computing platform, based either on dedicated Digital Signal Processing (DSP) units, general purpose CPUs, or, according to newer trends, Graphical Processing Units (GPU).

Figure 2A:
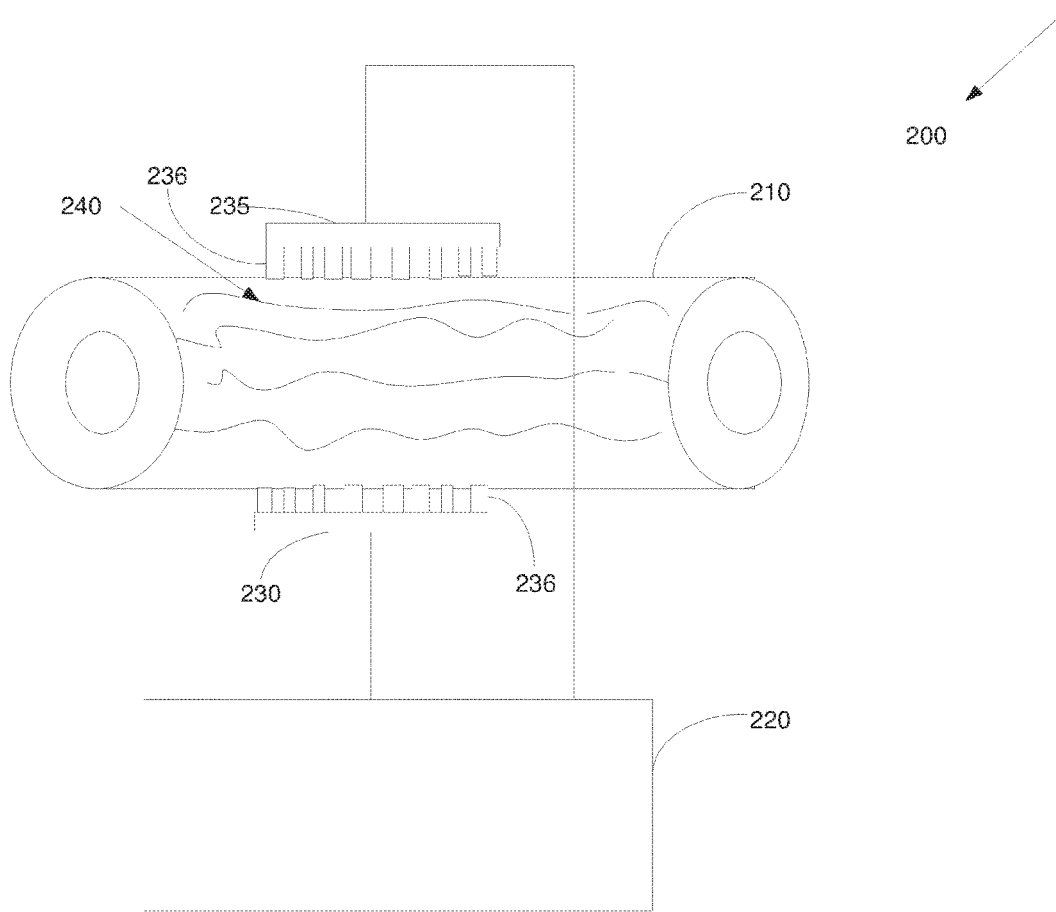
FIGS. 2A and 2B depicts the testing system including a capacitive sensor, according to an embodiment of the invention.

FIG. 2A illustrates another embodiment of a testing system 200 according to the invention. The testing system includes a container such as a pipe 210 for holding the OUT. A number of capacitive sensors such as two capacitive sensors 230 and 235 are connected to the container wall at multiple locations for spatially resolving the dielectric properties of the OUT. For example the capacitive sensor 235 is externally connected to one side of the pipe 210 while capacitive sensor 230 is externally connected to the other side of the pipe 210.

According to one embodiment of the invention, the capacitive sensors 235 and 230 may include a number of sensing lines such as feed lines 236 forming a mutual capacitance meter on the pipe. The feed lines 236 may be organized in a structure of but not limited to a grid. Additionally, the capacitive sensors 235 and 230 may include a plurality of sensing plates at the surface of the sensor, connected to the feed lines 236. Each of the feed lines is coupled to one or more corresponding receive lines through an electromagnetic field between at least two plates connected to said lines and to the OUT 240 located within the formed electromagnetic field in the pipe 210. In one embodiment, the sensors 235 and 230 may include a number of layers, where the feed lines 236, such as the column and row feed lines are placed in separate layers, and are connected to the sensing plates through vertical metalized holes (e.g. vias) interconnecting the layers. As shown in FIG. 2A the capacitive sensors 235 and 230 may be connected to the transmit/receive subsystem 220 for generation of signals to the capacitive sensors.

Figure 2B:
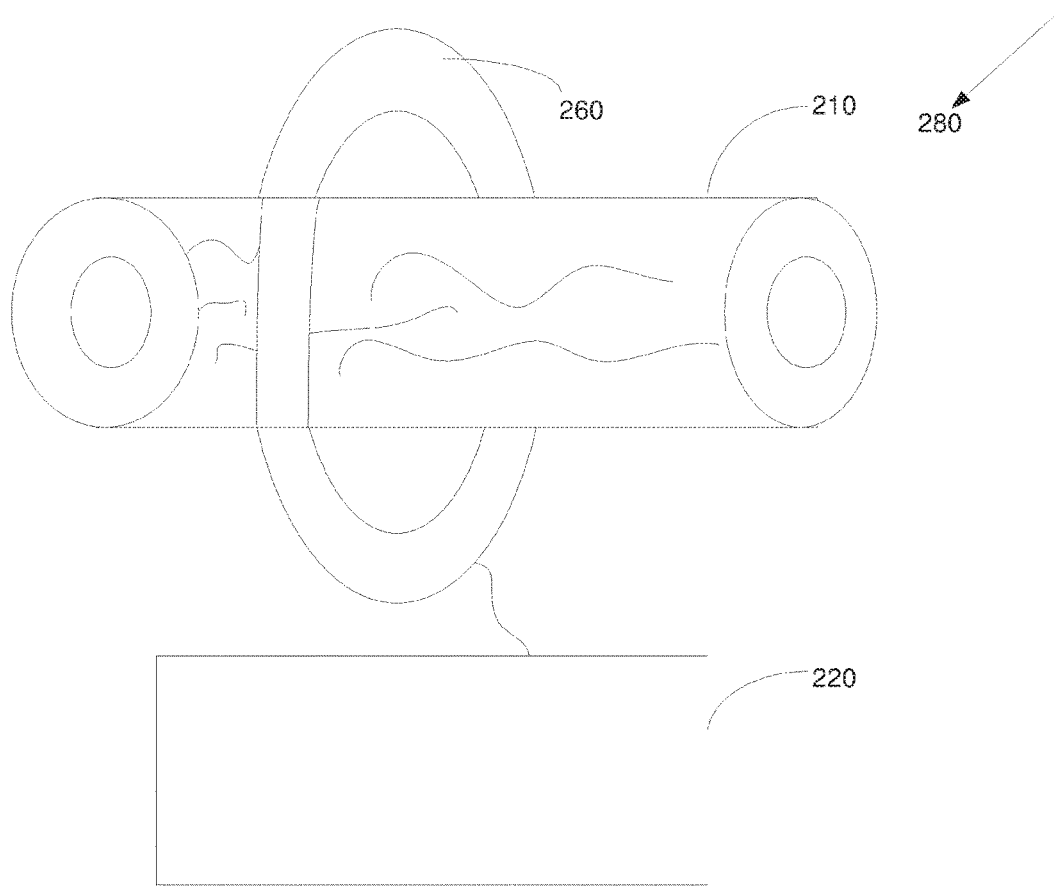

FIG. 2B illustrates another embodiment of a testing device 280 according to the invention. The testing device 280 may include a "ring shaped" capacitive sensor 260 surrounding the pipe 210. For example the capacitive may partially or completely surround the outside or inside walls of the pipe 210.

According to some embodiments of the invention as shown in FIG. 3 a testing device 300 may include a waveguide, such as waveguide 310. A waveguide is a structure that guides waves, such as electromagnetic waves or sound waves. As shown in FIG. 3 the waveguide 310 may be a hollow conductive metal pipe used to carry high frequency radio waves, such as microwaves 340 and the OUT 350. The waveguide may include a single wall or housing 315 or a number of walls to carry separately the OUT. The waveguide 310 may further include one or more connectors points such as connectors 325 connected to a transmit/receive subsystem 320 for generation of signals to the waveguide 310.

Figure 4:
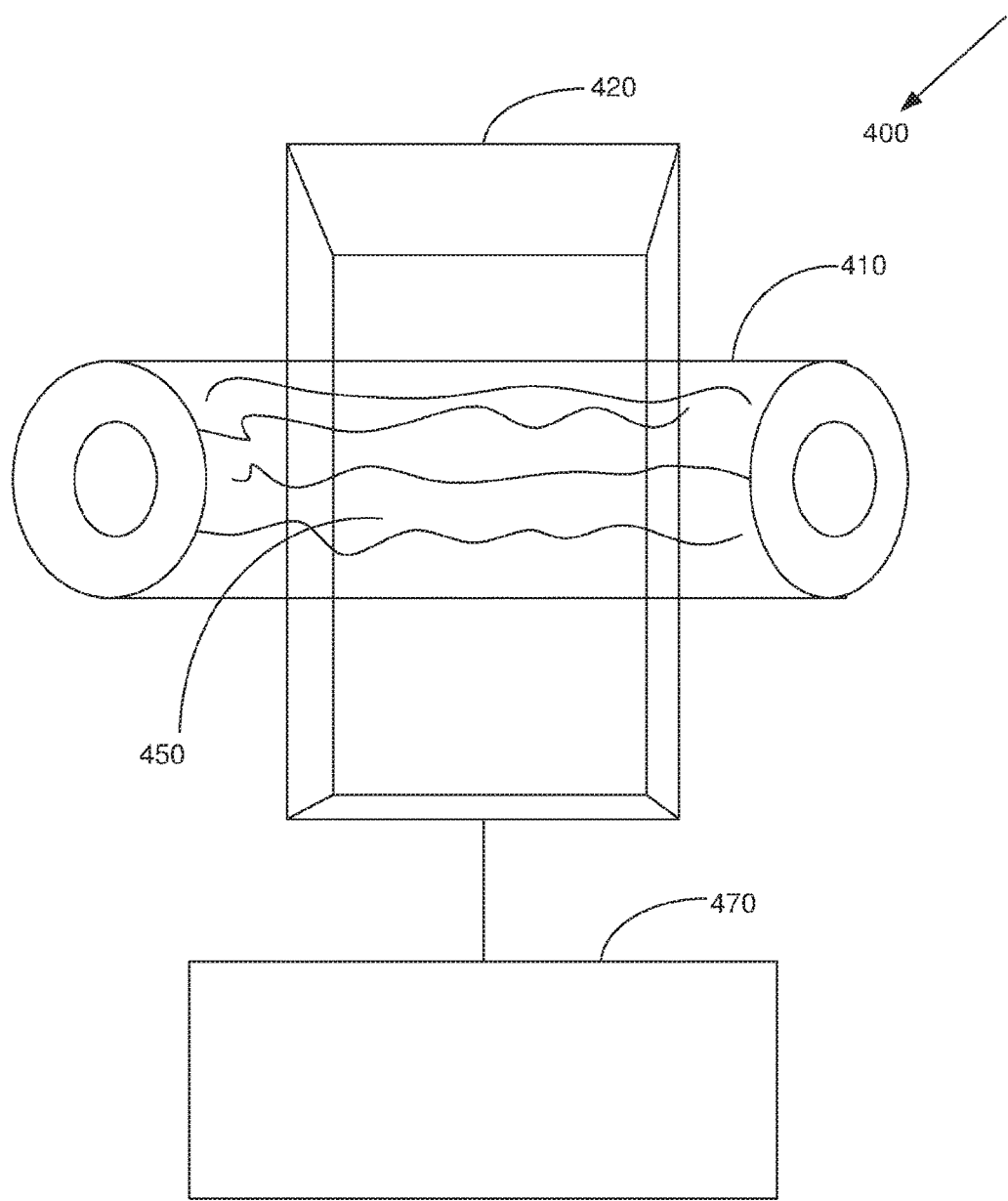
FIG. 4 depicts the testing system including a resonant cavity, according to an embodiment of the invention.

FIG. 4 illustrates another embodiment of a testing system 400. According to some embodiments of the invention, the testing system 400 may include a resonance cavity devise 420.

A resonant cavity is a cavity in which standing waves can be built up. For example, in a parallelepiped resonant cavity for electromagnetic waves as shown in FIG. 4, the $TE_{1mn}$ modes have:

$$B_z = B_{z_0} \sin\left(\frac{l\pi}{a}x\right)\sin\left(\frac{m\pi}{b}y\right)\sin\left(\frac{n\pi}{c}z\right)e^{-i\omega t} \quad (1)$$

$$E_t = \frac{1}{\gamma^2}\frac{i\omega}{c}\hat{z} \times \nabla_t B_z \quad (2)$$

$$B_t = \frac{1}{\gamma^2}\frac{\partial}{\partial z}\nabla_t B_z, \quad (3)$$

and the $TM_{1mn}$ modes have $$E_z = E_{z_0} \sin\left(\frac{l\pi}{a}x\right)\sin\left(\frac{m\pi}{b}y\right)\sin\left(\frac{n\pi}{c}z\right)e^{-i\omega t} \quad (4)$$

$$E_t = \frac{1}{\gamma^2}\frac{\partial}{\partial z}\nabla_t E_z \quad (5)$$

$$B_t = \frac{1}{\gamma^2}\frac{i\omega}{c}\hat{z} \times \nabla_t B_z. \quad (6)$$

Here, $$\gamma^2 \equiv \frac{\omega^2}{c^2} - k_z^2 \quad (7)$$

$$\nabla_t \equiv \hat{x}\frac{\partial}{\partial x} + \hat{y}\frac{\partial}{\partial y} \quad (8)$$

$$\frac{\omega^2}{c^2} = k_x^2 + k_y^2 + k_z^2. \quad (9)$$

As the resonance cavity has a large quality factor it will cause a wave to fade slowly if the cavity is empty and faster if the cavity includes a substance such as the OUT. As shown in FIG. 4 a container such as pipe 410 comprising the OUT 450 may he included in the resonance cavity 420. The resonance cavity 420 may be "box shaped" or have any shape configured to house the pipe 410. According to one embodiment of the invention the OUT ingredients such as abnormal milk ingredients may be identified according to cavity's resonance quality factor results and measured digression of the cavity resonance. The results may be transmitted in real-time or close to real-time to a user providing immediate "warning" on the stale milk.

According to another embodiment of the invention there is provided a system and method for testing of spillage such as liquid spillage, resulted for example of a gasoline pipeline or tank leakage.

Figure 5:
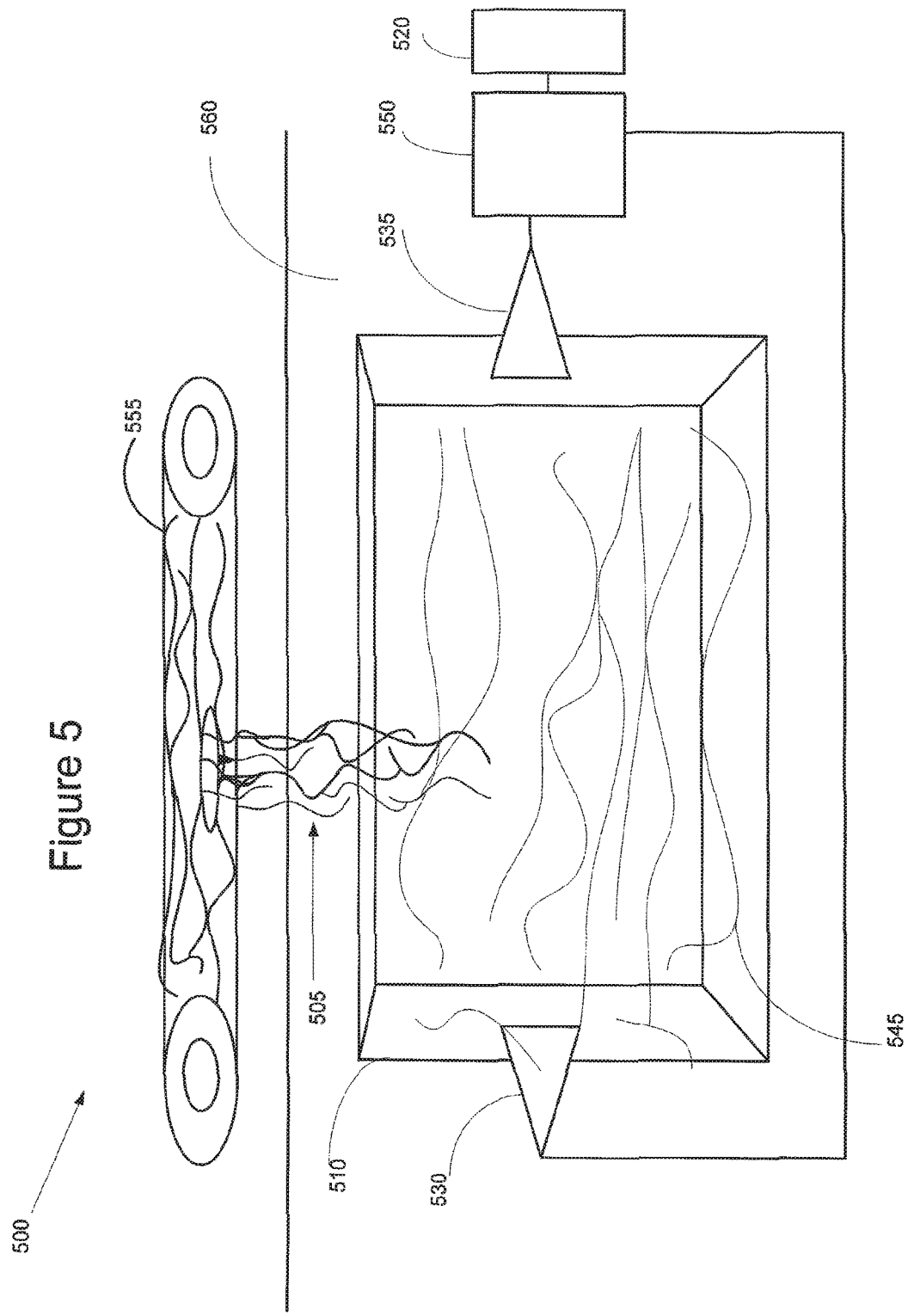
FIG. 5 depicts a testing system for testing a spillage, according to an embodiment of the invention.

FIG. 5 is an illustration of system 500 for characterizing a spillage 505, according to some embodiments of the invention. System 500 includes a sack 510 or a permeable tube filler made of for example fabric or any permeable material known in the art. The sack 510 further includes a granular material 545 such as sand and may be buried for example in the ground 560 below and/or in proximity of pipeline 555. The sack may include or may be connected to one or more microwave sensors such as antenna sensors 535 and 530. The sensors may transfer a plurality of RF signals propagating a wave into the sack 510 for testing the spillage 505. The sensors are further connected to a transmit/receive subsystem 550 for generation of signals to a Radio Frequency Signals Measurement Unit (RESMU) 520 such as a Vector Network Analyzer (VNA) 520 configured to receive and measure the received/reflected RF signals.

In operation, a gasoline leak in pipeline 555 cause gasoline to flow out of the pipeline, to the ground and into the sack 510. The spillage fills the air voids in the granular material 545 and changes the delay/loss properties of the granular material (i.e. the sand). Once a change in the granular material delay/loss properties is identified the system may automatically initiate an emergency process conveying an emergency message towards a pre-defined communication address reporting of gasoline pipeline leak.

Figure 6:
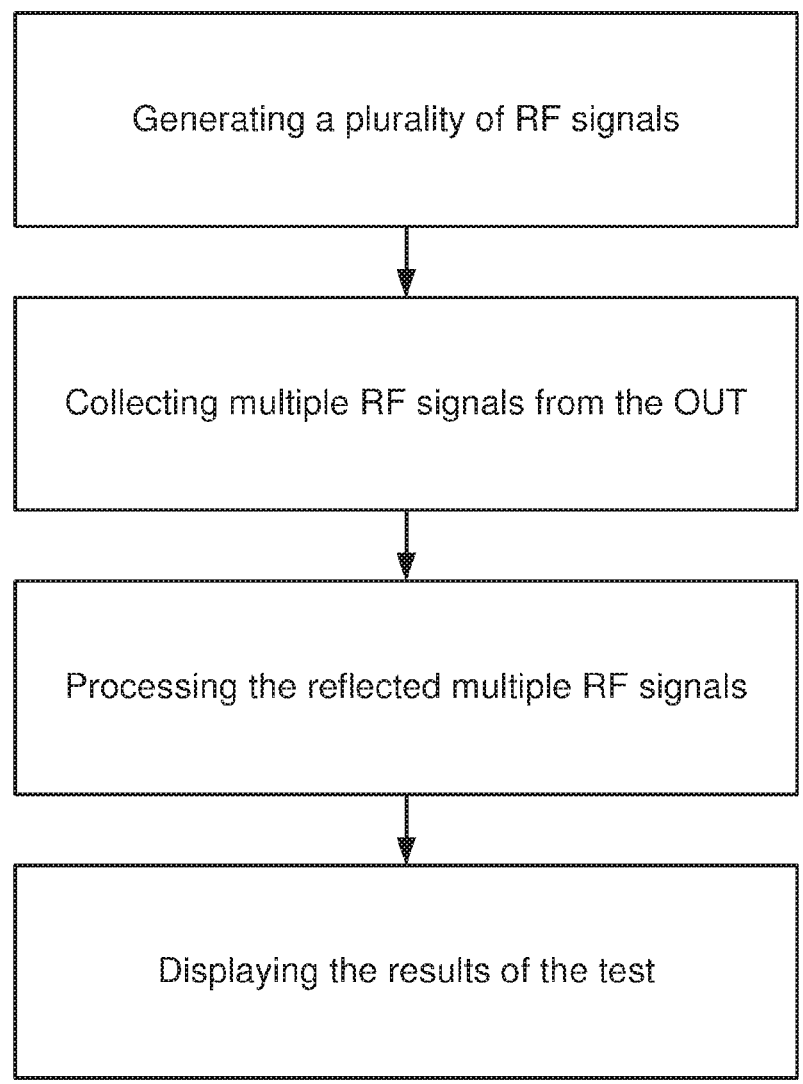
FIG. 6 is a flow chart of a method for testing an object according to an embodiment of the invention.

FIG. 6 is a flow chart of a method 600 for characterizing one or more substances according to an embodiment of the invention. The method begins in step 610 which includes generating a plurality of RF signals by a plurality of RF sensors externally attached to a container or sack comprising the substances (e.g. OUT). The RF sensors may be any of the mentioned above sensors.

Alternately Step 610 may be followed by inserting a granular material into the sack for collecting non-solid substances e.g. spillage resulted for example of a pipeline leak.

Step 620 includes collecting by the RF sensors multiple RF signals from the substances.

Step 630 includes processing the reflected multiple RF signals to measure the reflected RF signals for example according to impedance measures or dielectric properties of the substances and to identify the quantitative qualities of the substances. The processing step may be activated for example by a processor unit and a Radio Frequency Signals Measurement Unit (RFSMU) connected to the sensors. Step 640 includes displaying the results of the test for example presenting details on the detected mastitis or polluted substances.

The steps of the method of FIG. 6 (and its various alternatives) may be embodied in hardware or software including a non-transitory computer-readable storage medium (e.g., an optical disc or memory card) having instructions executable by a processor of a computing device.

In the above description, an embodiment is an example or implementation of the inventions. The various appearances of "one embodiment," "an embodiment" or "some embodiments" do not necessarily all refer to the same embodiments.

Although various features of the invention may he described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

What is claimed is:

1. A system for characterizing substances, said system comprising:
    a housing body having a cavity therein wherein said cavity is configured to contain said substances;
    a transmitter configured to transmit a plurality of Radio Frequency (RF) signals;
    at least one electromagnetic sensor in communication with said transmitter, wherein said at least one electromagnetic sensor is configured to provide RF responses data of said substances;
    a Radio Frequency Signals Measurement Unit (RFSMU) configured to receive said RF responses and measure said RF responses; and
    a processor connected to said at least one electromagnetic sensor said processor is configured to process said responses to identify characteristics of said substances, wherein said housing body comprises a granular material configured to receive said substance.

2. The system of claim 1, wherein said at least one electromagnetic sensor comprises at least two antennas and wherein said processor is configured to analyze a passage of energy transmitted from at least one of said antennas to at least one other antenna.

3. The system of claim 1, wherein said at least one electromagnetic sensor is a capacitive sensor and wherein said sensor is configured to spatially resolve dielectric properties of the substances.

4. The system of claim 3, wherein said capacitive sensor comprises:
    a plurality of sensing feed lines;
    a plurality of sensing plates; and
    a plurality of receive lines wherein each of said plurality of sensing feed lines is coupled to at least one corresponding receive line through an electromagnetic field formed between at least two sensing plates connected to said plurality of sensing feed lines and said plurality of receive lines and the substances.

5. The system of claim 1, wherein said at least one electromagnetic sensor is selected from the group consisting of: an antenna array, a MIMO radar sensor, resonant cavity sensor, microwave sensor, waveguide sensor.

6. The system of claim 5, wherein said MIMO radar sensor comprises a wideband antenna array connected to the transmitter, said transmitter is configured to generate microwave signals to said antenna array.

7. The system of claim 1, wherein said RF responses data comprises impedance measurements.

8. The system of claim 1, further comprising a tube wherein said tube comprises an inlet pipe and outlet pipe.

9. The system of claim 1, wherein said transmitter sensor is attached externally to the housing body walls.

10. The system of claim 1, wherein said transmitter sensor is attached internally to the housing body.

11. The system of claim 1, wherein said substances are selected from the group consisting of: liquid, paste, gas.

12. The system of claim 11, wherein said liquid is selected from the group consisting of: oil, milk, ink, water, bodily fluids.

13. The system of claim 1, wherein said transmitter sensor in not in direct contact with said substance.

14. A method for characterizing substances, said method comprising:
    obtaining multiple Radio Frequency (RF) signals from one or more RF sensors, said one or more RF sensors are attached to a housing body or to a cavity of said housing body wherein said cavity comprises a granular material configured to receive said substances;
    measuring the obtained multiple RF signals by a Radio Frequency Signal Measurement Unit (RFSMU), wherein said RFSMU is connected to said one or more RF sensors; and
    processing said measured RF signals by a processor to identify characteristics of said substances.

15. The method of claim 14, further comprising processing the obtained multiple RF signals to measure dielectric properties of said substances.

16. The method of claim 15, further comprising:
    comparing the dielectric properties of said substances to a predefined threshold reference to identify abnormal characteristics in said substances.

17. The method of claim 16, wherein the dielectric properties of the substances are spatially resolved.

18. The method of claim 14, wherein said substances are selected from the group consisting of: liquid, paste, gas.

19. The method of claim 18, wherein said liquid is selected from the group comprising: oil, milk, ink, water, bodily fluids.

20. The method according to claim 19, further comprising processing the dielectric properties of said substances to detect mastitis infection in the milk.

\* \* \* \* \*